United States Patent [19]

Cline et al.

[11] Patent Number: 4,699,877

[45] Date of Patent: Oct. 13, 1987

[54] METHODS AND COMPOSITIONS FOR DETECTING HUMAN TUMORS

[75] Inventors: Martin J. Cline, Pacific Palisades; Dennis J. Slamon, Woodland Hills, both of Calif.

[73] Assignee: The Regents of the University of California, Berkeley, Calif.

[21] Appl. No.: 673,469

[22] Filed: Nov. 20, 1984

Related U.S. Application Data

[63] Continuation-in-part of Ser. No. 439,252, Nov. 4, 1982, abandoned, and a continuation-in-part of Ser. No. 496,027, May 19, 1983, abandoned.

[51] Int. Cl.$^4$ .................... C12Q 1/68; G01N 33/53; C07K 7/00; A61K 39/00
[52] U.S. Cl. ........................ 435/6; 424/1.1; 424/9; 424/85; 435/7; 435/172.1; 436/503; 436/504; 436/508; 436/813; 530/326; 530/387; 530/403; 530/826; 530/828; 935/78; 935/81
[58] Field of Search .............. 435/172.1, 6, 7; 935/78, 81; 424/1.1, 9, 85; 436/503, 504, 508, 813; 260/112.5 R; 530/326, 387, 403, 826, 828

[56] References Cited

U.S. PATENT DOCUMENTS

| | | | |
|---|---|---|---|
| 4,331,647 | 5/1982 | Goldenberg | 424/1 |
| 4,348,376 | 9/1982 | Goldenberg | 424/1 |
| 4,358,535 | 11/1982 | Falkow et al. | 435/5 |
| 4,361,544 | 11/1982 | Goldenberg | 424/1 |
| 4,535,058 | 8/1985 | Weinberg et al. | 435/6 |

FOREIGN PATENT DOCUMENTS 2034323 6/1980 United Kingdom ............... 435/172

OTHER PUBLICATIONS

Stehelin et al, Chemical Abstracts, 94(1981) #27211x.
Tsuchida, Science, 217(1982) 937–938.
Hopp et al, Proc. Natl. Acad Sci. USA, 78(1981) 3824–3828.
Sutcliffe et al, Nature, 287(Oct. 30, 1980) 801–5.
Stehelin et al, Cold Spring Harbor Sympos. on Quant. Biol., vol. 44, pp. 12151–1223 (1980).
Heilmann et al, J. Virology, 24(1977) 498–504.
Shafritz et al, Hepatology, 1(1981).
Gowans et al, J. Med Virology, 8(1981) 67–78.
Petterson et al, J. Mol. Biol, 73(1973) 125–30.
Cronkite et al, Chem. Abstracts, 99(1983) #35338n.
Stone et al, Virology, 100(1980) 370–81.
Nevans et al, Adv. Virus Res, 26(1981) 1–35.
Herbrink et al, Cancer Res., 40(1980) 166–73.
Spector, Current Top. Microbiol. Immunol., 1981, 41–80.
Poiesz et al, Nature, 294(Nov. 19, 1981) 268–71.
Yoshida et al, Proc. Natl. Acad. Sci. USA, 79(1982) 2031–5.
Gallo et al, Proc. Natl. Acad. Sci. USA, 79(1982) 5680–3.
Essex, J. Natl. Cancer Inst., 69(1982) 981–5.
Wong-Staal et al, Science, 213(1981) 226–8.
Wong-Staal et al, Proc. Natl. Acad. Sci. USA 79(1982) 2490–4.
Microbiology, 3rd ed, Harper & Row, Philadelphia, 1980, 539–547; 1232–61.
Bishop, *Scientific American*, Mar. 1982, 81–93.
Bishop, *New England J. of Med.* (1980) 303:675–681.
*The Lancet*, Jul. 24, 1982, 195–196.
Cooper, *Science* (1982) 218:801–806.
Varmus, *Science* (1982) 216:812–820.
Becker et al., *Proc. Natl. Acad. Sci. USA* (1982) 79:3315–3319.
Tsuchida, *Science* (1982) 217:937–938.
Dhar, *Science* (1982) 217:934–936.

*Primary Examiner*—Christine M. Nucker
*Attorney, Agent, or Firm*—Bertram I. Rowland

[57] ABSTRACT

Methods and compositions for detecting the presence of tumors are provided, where a physiological sample is assayed for the expression product of a c-onc gene as diagnostic for the presence of the tumor. The method finds use in both pre- and postoperative situations with a host suspected of having transformed malignant cells.

22 Claims, No Drawings

METHODS AND COMPOSITIONS FOR DETECTING HUMAN TUMORS

RELATED APPLICATIONS

This application is a continuation-in-part application of copending application Ser. No. 439,252, filed Nov. 4, 1982, and copending application Ser. No. 496,027 filed May 19, 1983, now abandoned, incorporated herein by reference.

BACKGROUND OF THE INVENTION

1. Field of the Invention

The mechanism for malignancy of mammalian cells has been and continues to be the subject matter of intense investigation. One of the areas which is considered to be promising in the elucidation of the mechanism is the area of oncogenes. While the occurrence of oncogenes was first detected with retroviruses, it now seems reasonably firm that the viral oncogenes have cellular counterparts. The role of the cellular counterparts is not clear. An excellent review of oncogenes, their properties and particularly the src gene may be found in the article by J. Michael Bishop, Scientific American, Mar., 1982:81–93. The article also provides a list of various viral oncogenes, demonstrating that a number of them are involved with phosphorylation.

The src gene is found to be not only active in the malignant cell of chickens, but also in the normal cell. The difference appears to be one of degree, rather than of kind, in that the enzyme expressed by the src gene would appear to be of much higher concentration in the malignant cell as compared to the normal cell.

In order to be able to determine the presence of a tumor cell, it is necessary to be able to distinguish between normal cells and tumor cells. Therefore, the observed property which is to be diagnostic of the tumor cell must be capable of differentiation from a normal cell or from a physiologic fluid of a normal host, where the fluid rather than cells are assayed. Furthermore, the property should not be specific for the individual, but be common to the malignant nature of the cell.

In both diagnosis and treatment, the opportunity for specifically detecting malignant cells is very important. Any technique, in a high percentage of situations where malignancy is suspected, should be able to distinguish malignant cells from normal cells. Furthermore, the diagnostic technique should be useful for a large number of members of the population and not specific for one or a few members of the population.

Because a cancer cell is derived from a normal cell, most of the properties and components of the malignant cell are the same as the normal cell. Furthermore, there is an increasing view that malignancy is a result of a natural process, which in a certain context results in malignancy. In view of the fact that malignancy may be based on normal processes, which at the time in question have an aberrant result, it is not surprising that there has been substantial difficulty in demonstrating observable differences between normal cells and cancer cells over a broad spectrum of allogeneic hosts.

2. Description of the Prior Art

The following papers provide a general description of oncogenes and the role of retroviruses in tumorigenesis: Bishop, Scientific American, supra; Bishop, New England J. of Med. (1980) 303:675–681; Lancet, July 24, 1982, pages 195–196; Cooper, Science (1982) 218:801–806; Varmus, Science (1982) 216:812–820. Papers concerned with specific oncogenes include Becker et al., PNAS USA (1982) 79:3315–3319; Tsuchida et al., Science (1982) 217:937–938 and Dhar et al., ibid., (1982) 217:934–936.

SUMMARY OF THE INVENTION

Methods and compositions are provided for identifying and treating malignant cells of fresh tumors in a human host. From knowledge of DNA sequences capable of transforming cells of a lower vertebrate to malignancy, polynucleotide probes can be made for determining the level of transcription of said DNA in human cells and receptors produced capable of specifically recognizing determinant sites of peptide products of said DNA sequence. The probes and receptors may be labeled with a wide variety of labels for diagnosis and treatment.

DESCRIPTION OF THE SPECIFIC EMBODIMENTS

In accordance with the subject invention, novel methods and compositions are provided for the diagnosis and treatment of cancer in humans and other primates. It has now been observed that DNA which is capable of transforming cells of lower vertebrates to malignancy is present in human cells and has a much higher level of transcription and expression in malignant cells than in normal cells. Thus, by being able to detect the higher level of messenger RNA or the expression product of such messenger RNA, the presence of malignant cells in a host may be diagnosed. In addition, the production of the higher level of peptides in the malignant cells can be a basis for treatment of the malignancy. Where the polypeptide expression product can be found in physiological fluids, such as blood, and the levels of the expression product are substantially different in the presence and absence of malignancy, the physiological fluid may be screened as diagnostic for the presence of a particular tumor.

The subject invention provides methods and compositions for evaluating the probability or presence of malignant cells in a group of cells, particularly human cells in vivo or freshly removed from a human host. The method looks to cellular products such as mRNA or its expression product as diagnostic of the probable presence of malignant cells. The mRNA which is selected for detection will usually be selected as a result of there being RNA present in a retrovirus genome, which retrovirus is capable of transforming mammalian cells to malignancy. Furthermore, the RNA in the retrovirus which is selected is a sequence which does not encode an essential function of the retrovirus and, in fact, may be silent.

The method involves as a first step defining a DNA sequence capable of causing malignancy in a mammalian cell. Once the DNA sequence is defined, polynucleotide sequences can be provided which may serve as probes for detection of elevated levels of messenger RNA to determine whether a cell is malignant. The sequence can also be used for defining polypeptide sequences which can define complementary receptors having high specificity for the peptide sequence. The receptors may then be used for determining the presence or the concentration of the peptide in cells or physiological fluids and for treatment where the receptors can be directed to malignant cells. Also, knowing the nature of the peptide and its function, other means may be available for controlling the elevated production of the particular peptide.

The first step in the subject method is to define the DNA sequence. Various methods can be used for defining the DNA sequence of a retroviral oncogene. For example, retroviruses have been found capable of transforming lower vertebrate cells to malignancy. The retroviruses which have been characterized have been shown to carry DNA sequences comparable to wild type genes present in the host, genes which are now referred to as oncogenes. Furthermore, in the case of Rous sarcoma virus, the expression product of the gene has been isolated and characterized and shown to be a kinase. In the case of this kinase, it has also been shown that the kinase is normally produced by the cell, but at a much lower level than when the src gene from the Rous sarcoma virus is introduced. A number of viral oncogenes have already been detected in a variety of vertebrates, and the following is a list of the oncogenes and their species of origin.

TABLE 1

| Oncogene | Species of origin |
| --- | --- |
| v-src | chicken |
| v-fps | " |
| v-yes | " |
| v-fos | " |
| v-myc | " |
| v-erb | " |
| v-myb | " |
| v-rel | turkey |
| v-mos | mouse |
| v-bas | " |
| v-abl | " |
| v-ras | rat |
| v-fes | cat |
| v-fms | " |
| v-sis | monkey |

Other sources of DNA sequences capable of including malignant transformations in vertebrate cells may include isolated DNA from a malignant cell or cell line, cloned DNA from a genomic library or cloned DNA from a messenger RNA library, where the total messenger of the malignant cell is reverse transcribed to DNA and cloned. Either of these libraries may be screened for their ability to induce malignancy. A refinement in the technique of screening may be achieved by taking the total messenger from a normal cell and preparing cDNA from the messenger. One can then use the single stranded DNA as a probe to remove messenger RNA associated with the normal cell from the total messenger RNA from a malignant cell. The residual messenger RNA will then include messenger being expressed by genes associated with the malignancy. One may then use the messenger to screen a genomic library and use the cloned DNA which hybridizes with messenger in a bioassay for the determination of the ability to transform to malignancy. Other ways will also become available in time for detecting and defining DNA sequences capable of transforming normal cells.

A further analysis can be employed by screening cDNA from fetuses with messenger RNA from malignant cells. Particularly, where the oncogene is a gene which is silent or relatively quiescent in the mature vertebrate, while highly active in the embryo, the screening may further serve to narrow the field of sequences to be screened.

Once haVing identified a DNA sequence capable of inducing malignancy, a cloned viral oncogene or short polynucleotide sequences can be employed as probes for detection of the level of production of messenger RNA in cells suspected of being malignant. The preparation of both RNA and DNA nucleotide sequences, the labeling of the sequences, and the preferred size of the sequences has received ample description and exemplification in the literature. Normally, a sequence should have at least about 14 nucleotides, usually at least about 18 nucleotides, and the polynucleotide probes may be one or more kilobases. Various labels may be employed, most commonly radionuclides, particularly $^{32}P$. However, other techniques may also be employed, such as using biotin modified nucleotides for introduction into a polynucleotide. The biotin then serves as the site for binding to avidin or antibodies, which may be labeled with a wide variety of labels, such as radionuclides, fluorescers, enzymes, or the like. Alternatively, antibodies may be employed which can recognize specific duplexes, including DNA duplexes, RNA duplexes and DNA-RNA hybrid duplexes or DNA-protein duplexes. The antibodies in turn may be labeled and the assay may be carried out where the duplex is bound to a surface, so that upon the formation of duplex on the surface, the presence of antibody bound to the duplex can be detected.

By isolating the nucleotide sequence for the whole oncogene, the sequence of bases may be determined by known means, e.g. Maxam and Gilbert, PNAS USA (1977) 74:560. The sequence can be used for the determination of the amino acid sequence of the protein expressed by the oncogene. By identifying codons for methionine followed by a sequence which does not have stop codons which prevent expression, one can usually find a single sequence in frame with a methionine codon for defining the oncogene.

Alternatively, hybrid DNA technology may be employed for obtaining expression. The DNA sequence may be restriction mapped and appropriate sites for cleavage defined. In this way, the sequence may be excised and introduced into a vector having the appropriate regulatory signals. After obtaining expression of the DNA sequence, antibodies can be made to the polypeptide. By employing oocytes for expression of the messenger RNA which is then translated to produce the peptide expressed by the oncogene, the protein defined by the messenger may be produced. The identity of the peptide from the oocyte which the peptide produced by the expression of the hybrid DNA may then be determined.

Once the protein has been identified and verified, one can then use the protein or subunit peptides as an antigen for the production of antibodies for diagnosis and treatment. Antibodies can be prepared in a variety of ways, depending upon whether monoclonal or polyclonal antibodies are desired. For polyclonal antibodies, a vertebrate, normally a domestic animal, is hyperimmunized with the antigen and blood collected shortly after repeat immunizations and the gamma globulin isolated. For monoclonal antibodies, a small animal is hyperimmunized, the spleen removed and the lymphocytes fused with an appropriate fusing partner. The resulting hybridomas are then grown under limiting dilution and clones providing the desired antibodies selected.

Rather than preparing the entire peptide, one can determine various regions which are likely to be determinant sites and use these oligopeptides of at least about eight amino acids, usually at least about 10 and not more than 20, usually not more than 18 amino acids, to define a hapten which can be used to induce antibody formation. The oligopeptide is bound to an appropriate immunogen and introduced into a veterbrate to produce antibodies, either polyclonal or monoclonal antibodies, as described previously.

Accordingly, the present invention also provides a series of oligopeptides corresponding to antigenic regions in the peptide expression products of RNA present in retrovirus oncogenes. Exemplary species of the antigenic oligopeptides useful in accordance with the subject invention are listed below in groups based on the retroviral oncogene (expression product) which is recognized by antibodies produced from the oligopeptide.

A. Myb met-ala-phe-ala-his-asn-pro-pro-ala-gly-pro-leu-pro-gly-ala pro-phe-his-lys-asp-gln-thr-phe-thr-glu-tyr-arg-lys-met-his-gly-gly-ala-val pro-phe-his-lys-asp-gln-thr-phe-thr-glu-tyr-arg-lys-met asp-asn-thr-arg-thr-ser-gly-asp-asn-ala-pro-val-ser-cys-leu-gly-glu

B. Src arg-leu-ileu-glu-asp-asn-glu-tyr-thr-ala-arg-gln-gly-ala-lys-phe-pro trp-arg-arg-asp-pro-glu-glu-arg-pro-thr

C. Ras$^{Ki}$ arg-leu-lys-lys-ileu-ser-lys-glu-glu-lys-thr-pro-gly-cys-val-lys-ileu-lys-lys asp-leu-pro-ser-arg-thr-val-asp-thr-lys-gln-ala-gln-glu-leu-ala-arg met-thr-glu-tyr-lys-leu-val-val-val-gly-ala-ser-gly-val-gly-lys-ser-ala

D. Ras$^{Ha}$ glu-asp-ileu-his-gln-tyr-arg-glu-gln-ileu-lys-arg-val-lys-asp-ser-asp-asp val-arg-glu-ileu-arg-gln-his-lys-leu-arg-lys-leu-asn-pro-pro-asp-glu-ser-gly-pro met-thr-glu-tyr-lys-leu-val-val-val-gly-ala-gly-gly-val-gly-lys-ser-ala val-asp-glu-tyr-asp-pro-thr-ileu-glu-asp-ser-tyr-arg-lys-gln-val

E. Fes arg-his-ser-thr-ser-ser-ser-glu-gln-glu-arg-glu-gly-gly-arg asn-gln-gln-thr-arg-glu-phe-val-glu-lys-gly-gly-arg pro-glu-val-gln-lys-pro-leu-his-glu-gln ala-ser-pro-tyr-pro-asn-leu-ser-asn-gln-gln-thr-arg

F. Myc arg-leu-ileu-ala-glu-lys-glu-gln-leu-arg-arg-arg-arg-glu-gln-gln-gln-gln-gln-gln arg-leu-ileu-ala-glu-lys-glu-gln-leu-arg-arg-arg-arg-glu-gln asn-asn-glu-lys-ala-pro-lys-val-val In those situations where the human gene is different from the v-onc, e.g. human c-ras, the above described techniques may be used for isolating the gene, mRNA or pseudo-gene and obtaining antibodies to the human expression product. The human oncogene would be expected to have substantial complementarity to the related v-onc, normally differing in fewer than about 5% of the bases, generally differing by fewer than 5% of the amino acids in the expression product.

The antibodies may be used in a variety of ways. Particularly, they may be used for diagnosis. In instances where the antigen may be found in a physiological fluid at an elevated concentration only when malignancy exists, the physiological fluid, such as serum, plasma, whole blood or cerebrospinal fluid may be assayed. Antibodies employed in assays may be labeled or unlabeled. Unlabeled antibodies may be employed in agglutination; labeled antibodies may be employed in a wide variety of assays, employing a wide variety of labels, such as radionuclides, enzymes, fluorescers, enzyme substrates or cofactors, or the like. These techniques are amply defined in the literature and exemplary assays may be found in U.S. Pat. Nos. 3,817,834, 3,935,074, 4,233,402 and 4,318,980, as illustrative.

In some techniques, it will be useful to label the antigen or fragment thereof, rather than the antibody and have a competition between labeled antigen and antigen in the sample for antibody. In this situation, it is common to provide kits which have the combination of the labeled antigen or labeled fragment and the antibody in amounts which provide for optimum sensitivity and accuracy.

In other situations, it is desirable to have a solid support, where either antigen or antibody is bound. A polyepitopic antigen can serve as a bridge between antibody bound to a support and labeled antibody in the assay medium. Alternatively, one may have a competition between labeled antigen and any antigen in the sample for a limited amount of antibody.

Where the antigen may not be found in a physiological fluid or if found there is not diagnostic of malignancy, then cells will have to be isolated and the cells assayed for the presence of messenger RNA or the antigen. Methods of detecting messenger RNA have already been described. For detecting the antigen, the tissue sample may be lysed by conventional methods, e.g. base, detergents, or the like, cellular debris separated by filtration or centrifugation and the filtrate or supernatant isolated and assayed.

For purposes of therapy, either xenogeneic or allogeneic antibodies may be employed, depending upon the nature of the treatment, and whether the foreign antibodies will induce an immune response. The literature has described a number of ways of making human antibodies, where it is found that mouse or other mammalian antibodies are not satisfactory. The antibodies may be used in a wide variety of ways. By employing the appropriate IgG (other than IgG$_1$), one may induce lysis through the natural complement process. Alternatively, the lysing portion of a toxin may be joined to the antibodies, particularly a Fab fragment. The antibodies may be bound to liposomes for directing the liposomes to the malignant cells to become ingested by the cells by merging of the membranes. Other labels may also be bound to the antibodies, such as radionuclides, fluorescers, enzymes, and the like. By introducing the antibodies in vivo, the antibodies will direct the label to the malignant cell, where the presence of malignancy may be diagnosed or treated.

The formulation of the antibodies will vary widely, depending on the nature of the label, the purpose of the antibodies, the site to which the antibodies are to be directed, and the like. Usually, the antibodies will be formulated in a physiologically acceptable carrier, e.g. saline or phosphate buffered saline, and injected into the host, when possible at the desired site, and when this is not possible, into a circulating system, such as blood.

The antibodies obtained in accordance with this in-

Expression of 13 cellular oncogenes in 14 tumors was examined by DNA-RNA hybridization techniques. These data are summarized in Table 2.

TABLE 2

| | HUMAN MALIGNANCY* | | | | | | | | | | | | | |
|---|---|---|---|---|---|---|---|---|---|---|---|---|---|---|
| | GASTROINTESTINAL MALIGNANCIES Adenocarcinoma of | | | | RENAL CELL CARCINOMA | | | | OVARIAN CARCINOMA | | | LUNG ADENO- CARCINOMA | | LYMPHO- SARCOMA |
| V-ONC PROBE | Colon | | Small Bowel | Rectum | | | | | | | | | | |
| | 1 | 2 | 1 | 1 | 1 | 2 | 3 | 4 | 1 | 2 | 3 | 1 | 2 | 1 |
| Myc** | +++ | +++ | +++ | +++ | ++++ | ++++ | ++ | ++++ | ++ | ++ | ++ | ++ | ++ | − |
| Myb | − | − | − | − | − | − | − | − | − | − | − | − | ++ | − |
| Erb | − | − | − | − | − | − | − | − | − | − | − | − | − | − |
| Src | − | − | − | − | − | − | − | − | − | − | − | − | − | +++ |
| Yes | − | − | − | − | − | − | − | − | − | − | − | − | − | − |
| Abl*** | − | − | − | − | − | − | − | − | − | − | − | − | − | − |
| Fos | +++ | +++ | +++ | +++ | ++ | +++ | +++ | ++ | + | ++ | ++++ | + | ++ | − |
| Mos | − | − | − | − | − | − | − | − | − | − | − | − | − | − |
| Ras$^{Ha}$ | ++ | ++ | ++ | ++ | ++ | ++ | ++ | ++ | ++ | ++ | ++ | ++ | ++ | − |
| Ras$^{Ki}$ | ++ | ++ | ++ | ++ | ++ | ++ | ++ | ++ | ++ | ++ | ++ | ++ | ++ | − |
| Fes | − | − | − | − | − | − | − | − | − | − | − | + | ++ | − |
| Fms | − | − | − | − | − | − | − | − | − | − | − | − | − | − |
| Sis | − | − | − | − | − | − | − | − | − | − | − | − | − | − |

*Increasing numbers of pluses indicates increasing intensity of hybridization of tissue mRNA to v-onc probes.
**Avian
***Murine vention can also be used to isolate cells expressing the oncogene and to remove cells in vitro from a heterogeneous cell population containing cells expressing the oncogene. Separation can be achieved with a fluorescence activated cell sorter (FACS). This same technique can be used for identifying and isolating cells expressing the oncogene. For removing cells expressing the oncogene from a mixture of cells, the subject antibodies may be combined with complement, joined to the lysing fragment (A fragment) of a toxin (see E.P.O. application no. 17,507 and U.K. Patent Application No. 2,034,324) or the cells agglutinated and separated by physical means.

The following examples are offered by way of illustration and not by way of limitation.

Tumors were obtained from fresh surgical specimens at the time of resection and were untreated by chemotherapy or radiotherapy. An effort was made to obtain only viable tumor and to process the tissues as rapidly as possible to avoid messenger RNA (mRNA) degradation. Specimens were quickly frozen and stored in liquid nitrogen until processed for RNA. When the surgical specimens included wide margins of normal tissue, some of this was taken for analysis as an internal control of the level of c-onc gene expression. C-onc gene expression could then be compared in normal and malignant tissue from the same patient. As little as 20 pg of Maloney murine sarcoma virus equivalent to approximately one RNA transcript of 3 kilobases (kb) per cell or approximately 2 micrograms of poly A RNA applied to the filter could be detected by this method (Kafatos et al., Nucleic Acids Res. (1979)7:1541). By use of appropriate controls including unrelated RNA's, poly A-negative fraction RNA, plasmid DNA, and mouse and human DNA, false-negative as well as false-positive results could reasonably be excluded. The dot blots were quantitatively evaluated by means of a soft laser scanning densitometer. Where sufficient material was available, mRNA was further characterized by Northern analysis to confirm the presence of, and to size, specific transcripts (Thomas, PNAS USA (1980)77:5201).

Three patterns were observed: (1) expression of specific c-onc mRNA sequences in all or nearly all tumor samples (e.g., c-myc); (2) detection of c-onc expression in sporadic tumors (e.g., c-fes); and (3) no detectable expression (e.g., c-mos).

No significant expression of mRNA sequences homologous to c-erb, c-yes, c-abl, c-mos, c-fms, or c-sis could be detected. This was not the result of lack of homology between the viral gene probe and the human messenger RNA, since it was possible to detect homologues of all these probes in human genomic DNA. RNA from microscopically normal tissue did not contain any detectable transcripts by this analysis.

Four cellular oncogenes showed a consistent pattern of expression in a variety of human tumors. These were c-myc, c-fos, c-ras$^{Ha}$, and c-ras$^{Ki}$. A comparison was made of the intensity of hybridization, which was possible since all probes were labeled to approximately the same specific activity. V-myc and v-fos demonstrated the highest intensity of hybridization to human tumor RNA's, suggesting a large number of copies of mRNA per cell. Expression of both these genes was observed in all malignancies examined. C-ras$^{Ha}$ and c-ras$^{Ki}$ sequences were also detected in most of the human tumors but with less intense hybridization.

Messenger RNA sequences related to c-fes were detected in only 2 of 14 tumors examined; both of these were lung cancers.

C-myb expression was detected in only one of 14 tumors; this, too, was a lung cancer.

C-src messenger RNA sequences were observed only in circulating tumor cells of a patient with lymphosarcoma.

In order to test whether expression of cellular oncogene sequences was related to neoplasia, an effort was made to obtain both grossly normal-appearing tissue and obviously malignant tissue from the same site in the same patient at the same time. Hybridization studies were then performed on RNA samples from the tumor and from adjacent noninvolved tissues. In 6 of the 14 patients it was possible to perform this analysis. In 1 of these 6 cases the presumed normal tissue was subsequently shown by histologic analysis to be infiltrated by tumor. In 4 of the remaining 5 cases there was differential expression between the tumor and normal tissue, with low or undetectable levels observed in the normal tissues and elevated levels observed in the malignancy. Three of the renal cell carcinomas and one colon carcinoma demonstrated this phenomenon.

Blot analysis of RNA from cells in the areas of the tumor sample and the control sample showed a correlation between the presence or absence of tumor and c-onc gene expression. In one tumor, an adenocarcinoma of the small bowel, c-onc-related sequences were found in histologically normal adjacent tissue.

Analyses of poly A RNA from tumors and control tissues were performed by the Northern technique. Two c-myc-related transcripts of 4.0 and 2.0 kb were found in all tumors examined. In addition to these transcripts, there was obvious degradation of some of the messenger RNA in these hybridization analyses, most likely resulting from degradation occurring during tissue anoxia in the period after surgical removal of the tissue.

Using the procedures given above, several other tumor types obtained from fresh surgical specimens were examined for c-onc gene expression. In this series of tests, DNA-RNA hybridization was used to look for expression of 10 different cellular oncogenes in 9 tumors. The data obtained are summarized in Table 3 below.

size prior to day 10 prevented separation and therefore the embryos of days 6–9 represent the entire conceptus as dissected from the uterine wall.

Aliquots of poly(A)-containing RNA (poly(A+) RNA), were isolated by affinity chromatography on oligo(dT)-cellulose columns and spotted on nitrocellulose paper (dot blots) (Kafatos et al., Nucl. Acids Res. (1979) 7:1541-1552). The samples were hybridized to [$^{32}$P]-labeled molecularly cloned oncogene-specific probes. Dot blots were quantitatively evaluated by means of a soft laser scanning densitometer. Transcriptional activity of c-onc's was additionally studied in more detail in various tissues of newborn and 10 day old mice. Agarose gel electrophoresis followed by blotting on nitrocellulose paper (Northern blotting), (Thomas, PNAS USA (1980) 77:5201–5205) was used to confirm the results obtained by dot blot analysis and additionally to determine the sizes of the different c-onc-related transcripts.

More specifically, RNA was isolated from Swiss-Webster mouse embryo fetuses at various stages of development using the guanidine thiocyanate method. (Cox, Methods Enzymol. (1967) 12:120–129; Adams et al., PNAS USA (1980) 74:3399–3043).

As indicated above, days 6–9 Swiss-Webster mouse embryos represent the entire conceptuses including all extraembryonal tissues, such as membranes and those cells giving rise to the placenta at later developmental stages. At all later stages, the embryo proper was dis-

TABLE 3

| | HUMAN MALIGNANCY* | | | | | | | | |
|---|---|---|---|---|---|---|---|---|---|
| V-ONC | BREAST CARCINOMA | | | UTERINE CARCINOMA | THYMOMA | HODGKIN'S | NON-HODGKIN'S LYMPHOMA | CHRONIC MYELOCYTIC LEUKEMIA | |
| PROBE | 1 | 2 | 3 | 1 | 1 | 1 | 1 | 1 | 2 |
| Myc** | ++ | +++ | +++ | − | + | ++ | + | ++ | − |
| Myb | + | ++ | − | − | − | + | − | + | − |
| Src | + | + | − | − | − | ++ | + | +++ | − |
| Rel | − | − | − | − | − | − | − | − | − |
| Abl*** | − | − | − | − | − | − | − | − | − |
| Fos | ++ | ++ | ++ | − | + | ++ | + | ++++ | ++++ |
| Ras$^{Ha}$ | +++ | +++ | +++ | − | + | ++ | + | ++ | + |
| Ras$^{Ki}$ | + | + | ++ | − | − | + | − | + | + |
| Fes | + | ++ | +++ | − | − | + | + | +++ | ++ |
| Sis | − | − | − | − | − | − | − | − | − |

*Increasing numbers of pluses indicates increasing intensity of hybridization of tissue mRNA to v-onc probes.
**Avian
***Murine The results given in Table 3 correlate fairly well with the results previously reported in Table 2 in that the cellular oncogenes c-myc, c-fos, c-ras$^{Ha}$, and c-ras$^{Ki}$ show a consistent pattern of expression in the additional tumor types examined. Further, c-myb, c-src and c-fes were also detected in several additional tumor types whereas c-rel, c-abl and c-sis expression was not observed in any of the additional tumor types examined. Interestingly, none of the cellular oncogenes looked for were found to be expressed at any significant level in the single uterine carcinoma evaluated.

To determine whether the messenger RNA shown to be present in malignant cells in elevated amounts were related to genes involved in embryogenesis, experiments were carried out generally as follows. Total RNA was isolated from embryo/fetuses of random-bred Swiss mice at daily intervals starting on the 6th day of gestation (day of coital plug was taken as day 0 of prenatal development). Beginning at day 10 of prenatal development, the embryo proper was separated from the extraembryonal membranes and placenta. The small sected free of extraembryonal tissues. RNA was selected for poly(A+)-RNA by one cycle of chromatography on oligo(dT)-cellulose columns (Aviv and Leder, PNAS USA (1972) 69:1408–1412). Poly(A+)-RNA was dissolved in water, boiled, quick-cooled on ice and 3 μg-(1.5 μl) were applied to sheets of nitrocellulose paper which had previously been equilibrated with 20×SSC (1×SSC is 0.15 NaCl, 0.015M sodium citrate) and air dried. After baking overnight at 80° C., the blots were prehybridized for at least 4 h at 45° C. in a buffer containing 0.75M NaCl, 0.05M sodium phosphate (pH7.5), 0.005M EDTA, 0.2% SDS, 10 mg of glycine/ml, 5×Denhardt's reagent (1×Denhardt's reagent is 0.02% each of ficoll, bovine serum albumin and polyvinylpyrrolidone), 0.25 mg of denatured herring DNA/ml and 50% formamide.

The blots were hybridized for about 20 h at 45° C. with 1×10$^6$ cpm of nick-translated probe/ml of hybridization buffer (prehybridization buffer with Denhardt's reagent at 1×). The cloned oncogene fragments purified from vector sequences by preparative agarose gel electrophoresis were nick-translated (Rigby et al., J. Mol. Biol. (1977) 113.237–251) in the presence of [$^{32}$P]-dCTP(3200 Ci/mmol) to specific radioactivities of about $1-2\times 10^9$ cpm/μg of DNA. After hybridization, the blots were washed three times in 1×SSC at 50° C. for a total of about 2 h and exposed to preflashed X-ray films with intensifying screens at −70° C. for 72 h.

Employing the above procedure, a number of known oncogenes were screened to determine whether they were expressed in the embryos. The following table indicates the individual oncogene and the observations concerning their expression in embryonic cells.

TABLE 4

| Oncogene | Virus | Disease | mRNA production embryos days 6–9 | 10–18 | fetus |
|---|---|---|---|---|---|
| fos[1] | FBJ-osteosarcoma | osteosarcoma | + | − | + |
| abl[2] | Abelson leukemia | lymphoma | + | + | + |
| ras$^{Ha}$[3] | Harvey sarcoma | erythroleukemia, sarcoma | + | + | + |
| mos[4] | Maloney sarcoma | sarcoma | − | − | − |
| myc[5] | Avian myelocytomatosis | carcinoma, sarcoma leukemia | + | + | |
| erb[6] | Avian erythroblastosis | leukemia, sarcoma sarcoma | − | + | |
| src[7] | Rous sarcoma virus | sarcoma | + | + | |
| myb[8] | Avian myeloblastosis | leukemia | − | − | |
| fes[9] | Snyder-Theilin feline sarcoma | sarcoma | − | − | |
| sis[10] | Simian sarcoma | sarcoma | + | + | |

[1] Curran et al., J. Virol. (1982)
[2] Goff et al., Cell (1980) 22:777–785
[3] Ellis et al., J. Virol. (1980) 36:408–420
[4] Oskarsson et al., Science (1980) 207:1222–1227; Jones et al., PNAS USA (1980) 77:2651–2655
[5] Eva et al., Nature (1982) 295:116
[6] Gonda et al., Mol. Cell. Biol. (1982) 2:617
[7] Wang et al., (1977) J. Virol. 24:64
[8] Vister et al., PNAS USA (1982) 79:3677–3681
[9] Fedele et al., PNAS (1982), in press
[10] Devare et al., PNAS (1982) 79:3179–3182

Relatively high levels of c-fos related sequences were detected in poly(A+)-RNA prepared from 6, 7, 8 and 9 day conceptuses containing the embryo proper and extraembryonal tissues. More than 10-fold lower fos expression was observed in embryos of later development stages dissected free of extraembryonal tissues. Data from the placenta and extraembryonal membranes of fetuses from days 10 to 18, showed that expression was primarily in those tissues. In postnatal tissue, c-fos expression could be observed in all tissues investigated with stronger hybridization to the fos-specific probe from bones.

Hybridization showed that for c-abl about three-fold higher levels in the embryo proper than in extraembryonal membranes and placenta is observed at the 10th day of gestation, as compared to the concentration observed in the 6, 7, and 9 day conceptuses. Expression of c-abl in the fetus appears to decrease after the 11th day of prenatal development. The oncogene c-abl is transcriptionally active in all postnatal mouse tissues examined with spleen and thymus poly(A)+ RNA exhibiting a slightly stronger hybridization than from other tissues.

The oncogene c-ras$^{Ha}$ was found to be expressed in considerable, but similar levels at all stages of prenatal development both in the embryo proper as well as in extraembryonal tissues. High levels of c-ras$^{Ha}$ expression were also observed in various tissues of newborn or 10 day old mice, particularly in bone, brain, kidney, skin and spleen.

The oncogene c-myc was detectable at days 7 and 8, but much higher levels were observed in late embryonic development (days 17 and 18).

The oncogene c-erb had maximum hybridization at 13 days, while no hybridization was observed at day 6.

The oncogene c-src was detected at its highest levels in the latter half of mouse embryonic development with an increase beginning at day 14, peaking at day 15 and gradually decreasing thereafter. For the oncogene c-sis, peak expressions were observed at days 7 and 16, the day-7 peak was 1.5 to 3 times higher than all other days and the day-16 peak was 1.5 to 2 times higher than days 9 to 13 and days 17 and 18.

In the next study, the nucleotide sequence of the presumed oncogene region of Avian myeloblastosis virus myb was employed (Vister et al. (1982) supra). Using the published nucleotide sequence, a number of antigenic oligopeptide sequences were derived and seven of the polypeptides so derived were synthesized and evaluated as being potentially antigenic. These seven oligopeptides, which are representative antigenic oligopeptides according to the invention, have the following formulas:

(1) pro-phe-his-lys-asp-gln-thr-phe-glu-tyr-arg-lys-met
(2) pro-ser-pro-pro-val-asp-his-gly-cys-leu-pro-glu-glu-ser-ala-ser-pro-ala-arg
(3) asp-asn-thr-arg-thr-ser-gly-asp-asn-ala-pro-val-ser-cys-leu-gly-glu
(4) pro-gln-glu-ser-ser-lys-ala-gly-pro-pro-ser-gly-thr-thr-gly
(5) met-ala-phe-ala-his-asn-pro-pro-ala-gly-pro-leu-pro-gly-ala
(6) pro-pro-val-asp-his-gly-cys-leu-pro-glu-glu-ser-ala-ser-pro-ala
(7) pro-phe-his-lys-asp-gln-thr-phe-thr-glu-tyr-arg-lys-met-his-gly-gly-ala-val The polypeptides were linked to keyhole limpet hemocyanin in accordance with conventional techniques (Dockray, Regulatory Peptides (1980)1:169) and the resulting immunogen was used to immunize rabbits in a first injection with complete Freund's adjuvant, followed by injections with incomplete Freund's adjuvant over periods of three to four weeks to hyperimmunize the rabbits. The rabbits were bled repeatedly over a period of six months. Of the seven oligopeptides which resulted in the production of antibodies, antibodies to two peptides (5 and 7) were selected for detailed analysis. The antibodies were reacted with radioactively labeled cell lysates from a cell line containing multiple copies of the Avian myeloblastosis virus and with lysates from appropriate non-infected cell lines. Antibody No. 5 identifies a specific protein of approximately 58,000 daltons, which is present in the virus-infected cell line but not in controls.

Antibody against polypeptide 5 was also reacted with the plasma of chickens bearing tumors induced by amv. A band similar to that observed with the above lysates of approximately 48,000 daltons was identified.

Antisera to polypeptide No. 5 was also reacted with lysates of a myeloid human leukemia cell line (HL-60) which is known to express messenger RNA transcripts of the c-myb gene (Gallo and Wong-Staal, Blood (1982) 60:545). This antibody reacted with a protein of about 90,000 daltons. In freshly isolated myeloid leukemia cells, the antibody identifies a series of proteins, 14 kd to 70 kd, not present in normal white blood cells.

The polyconal antibodies to the fragment no. 5 of the myb protein was tested for its ability to kill normal and leukemic cells. The procedure employed is described in Terasaki and McClelland, infra. The data are set forth in the following table.

whole protein, particularly with the whole protein in a membrane. The subject antibodies can be used to select for antibodies binding to the same or other determinant site.

The subject data demonstrate that antibodies can be prepared which do not affect normal B- and T-cells, but are cytotoxic in combination with complement for a variety of malignant cells. Therefore, the antibodies can be used for cancer therapy without the hazard of substantially inactivating the immune system.

It is evident from the above results, that one can detect the presence of malignancy in a human host by determining the transcription and/or expression products of the oncogene. One can screen retroviruses or other source of nucleic acids to transform vertebrates to malignancy. One may then use these nucleic acids to deduce peptide composition and screen malignant cells for transcripts or peptides, by hybridization in the former case and with appropriate receptors in the latter case, employing any of a wide variety of diagnostic assays. Antibodies can be produced to the peptides, which antibodies may be labeled and may then be used for diagnosing the presence of a peptide diagnostic of malignancy. The oncogenic proteins are found to be available for binding to antibodies as surface membrane proteins. The antibodies may serve as diagnostic reagents for determining the presence of malignancy and determining the location of malignant cells. The antibodies may also serve in treating tumors in vivo by using radionuclides, toxins, in combination with the host complement system or opsonins, or other antibody dependent lytic system or the like. The antibodies find

TABLE 5

CYTOTOXICITY* OF ANTI-Myb2 ANTIBODY AGAINST HUMAN CELLS

| Antiserum | Dilution | Cells[++] | | | | | | | | |
|---|---|---|---|---|---|---|---|---|---|---|
| | | Normal B | Normal T | Molt 4 (T) | HL-60 (AML) | Common ALL 1 | Common ALL 2 | AML (5)** | T-ALL 1 | T-ALL 2 |
| Medium Alone (−control) | | 1 | 1 | 1 | 1 | 1 | 1 | 1 | 1 | 1 |
| ALS[+] (+control) | — | 8 | 8 | 8 | 8 | 8 | 8 | 8 | 8 | 8 |
| Anti-myb | — | 1 | 1 | 8 | 6 | 6 | 1 | 6 | 6 | 6 |
| | 1:2 | 1 | 1 | 6 | 1 | 1 | 1 | 6 | 6 | 2 |
| | 1:4 | 1 | 1 | 6 | 1 | 1 | 1 | 4 | 4 | 1 |
| Pre-immune | — | 1 | 1 | 4 | 1 | 1 | 1 | 1 | 4 | 2 |
| | 1:2 | 1 | 1 | 2 | 1 | 1 | 1 | 1 | 2 | 2 |
| | 1:4 | 1 | 1 | 2 | 1 | 1 | 1 | 1 | 2 | 2 |

*8 = 80–100% killing 6 = 60–80% killing 1 = 0–10% killing
The method of Terasaki and McClelland, Nature (1964) 204:998, was employed for complement lysis.
**3 of 5 are killed; a representative one is shown
[+] ALS - antileukocyte serum
[++] Molt 4 is a non-malignant human T lymphoid cell line that is known to express myb nRNA.
HL-60 - human myeloid leukemia cell line
AML - acute myeloid leukemia
ALL - acute lymphocyte leukemia
T-ALL - T-cell acute lymphoblastic leukemia The above results demonstrate that the expression product of the myb gene can react with antibodies to produce lysis with complement. Thus, the myb protein appears to be a surface membrane protein which is available for binding to antibodies. By identifying proteins to which specific antibodies will bind, which proteins have diagnostic value as indicative of malignance, the malignant cells can be identified and treated. In the subject work, no determination has been made as to the specificity or cross-reactivity of the subject antibodies. Since only a fragment was used to prepare the antibodies, it would be expected that antibodies of greater binding specificity and avidity could be prepared with the use in pre- and postoperative systems, in the latter determining whether complete removal has occurred, whether metastases exist. The antibodies can be used postoperatively to destroy any remnants of the tumor which may not have been excised.

Although the foregoing invention has been described in some detail by way of illustration and example for purposes of clarity of understanding, it will be obvious that certain changes and modifications may be practiced within the scope of the appended claims.

What is claimed is:

1. A method for evaluating the probability of cellular malignancy in a human host, said method comprising:
   bringing into close association (1) a probe specific for a cellular product, said cellular product being mRNA or its expression product, where said mRNA is complementary to a DNA sequence of a retrovirus capable of transforming a normal cell to malignancy and said probe is a nucleic acid sequence capable of duplexing with said mRNA or antibody capable of binding to said expression product, and (2) a source from said human host suspected of containing cellular product; and
   determining the level of binding of said probe to said cellular product, wherein an elevated level is indicative of the presence of cellular malignancy.

2. A method according to claim 1, wherein said source is cells from said human host.

3. A method according to claim 1, wherein said source is a physiological fluid from said human host.

4. A method according to claim 1, wherein said DNA sequence is selected from the group consisting of the oncogenes src, fps, yes, fos, myc, erb, myb, rel, mos, bas, abl, ras, fes, fms, and sis.

5. A method according to any of claims 1, 2, 3, or 4, wherein said probe is an antibody.

6. A method according to claim 5, wherein said antibody is labeled with a label capable of providing a detectible signal.

7. A method according to any of claims 1, 2, 3, or 4, wherein said probe is a polynucleotide of at least 14 bases complementary to said mRNA.

8. A method for evaluating the probability of leukemia in a human host, said method comprising:
   combining antibodies specific for the oncogene myb and blood cells from a human host suspected of having leukemia; and
   determining the level of binding of said antibodies to said host blood cells as diagnostic of a leukemic host.

9. A method according to claim 8, wherein said antibodies are produced in response to an oligopeptide mimicking a portion of the conformation of the myb protein.

10. A method for substantially eliminating human malignant cells from a combination of human malignant and normal cells, which comprises:
    combining under cytotoxic conditions said combination of cells with an antibody specific for an expression product of a DNA sequence present in a retrovirus genome or substantially complementary to said DNA sequence, which sequence is expressed in said malignant cells as a surface protein; and
    isolating normal cells, substantially free of malignant cells.

11. A method according to claim 10, wherein said separation occurs in the presence of complement as said cytotoxic condition.

12. A method according to claim 10, wherein said antibodies are labeled with a radionuclide as said cytotoxic condition.

13. A method according to any of claims 10, 11, or 12, wherein said DNA sequence is the myb gene.

14. A method for treating a human host suspected of having malignant cells, which comprises:
    administering to said human host under cytotoxic conditions antibodies to the expression product of a gene, which gene is part of a retrovirus genome capable of inducing malignancy in a normal cell or which gene is substantially complementary to said gene of said retrovirus genome.

15. A method according to claim 14, wherein said cytotoxic condition is the presence of complement.

16. Antibodies specific for the expression product of the human oncogenes c-myc, c-fos, c-ras$^{Ha}$, c-ras$^{Ki}$, c-fes, c-myb, and c-src.

17. Antibodies according to claim 16, labeled with a label capable of providing a detectible signal.

18. Antibodies according to claim 16, labeled with a cytotoxic agent.

19. An antigenic oligopeptide selected from the class consisting of:
(a) met-ala-phe-ala-his-asn-pro-pro-ala-gly-pro-leu-pro-gly-ala
(b) pro-phe-his-lys-asp-gln-thr-phe-thr-glu-tyr-arg-lsy-met-his-gly-gly-ala-val
(c) pro-phe-his-lys-asp-gln-thr-phe-thr-glu-tyr-arg-lys-met
(d) asp-asn-thr-arg-thr-ser-gly-asp-asn-ala-pro-val-ser-cys-leu-gly-glu
(e) arg-leu-ileu-glu-asp-asn-glu-tyr-thr-ala-arg-gln-gly-ala-lys-phe-pro
(f) trp-arg-arg-asp-pro-glu-glu-arg-pro-thr
(g) arg-leu-lys-lys-ileu-ser-lys-glu-glu-lys-thr-pro-gly-cys-val-lys-ileu-lys-lys
(h) asp-leu-pro-ser-arg-thr-val-asp-thr-lys-gln-ala-gln-glu-leu-ala-arg
(i) met-thr-glu-tyr-lys-leu-val-val-val-gly-ala-ser-gly-val-gly-lys-ser-ala
(j) glu-asp-ileu-his-gln-try-arg-glu-gln-ileu-lys-arg-val-lys-asp-ser-asp-asp
(k) val-arg-glu-ileu-arg-gln-his-lys-leu-arg-lys-leu-asn-pro-pro-asp-glu-ser-gly-pro
(l) met-thr-glu-tyr-lys-leu-val-val-val-gly-ala-gly-gly-val-gly-lys-ser-ala
(m) val-asp-glu-tyr-asp-pro-thr-ileu-glu-asp-ser-tyr-arg-lys-gln-val
(n) arg-his-ser-thr-ser-ser-ser-glu-gln-glu-arg-glu-gly-gly-arg
(o) asn-gln-gln-thr-arg-glu-phe-val-glu-lys-gly-gly-arg
(p) pro-glu-val-gln-lys-pro-leu-his-glu-gln
(q) ala-ser-pro-tyr-pro-asn-leu-ser-asn-gln-gln-thr-arg
(r) arg-leu-ileu-ala-glu-lys-glu-gln-leu-arg-arg-arg-arg-glu-gln
(s) asn-asn-glu-lys-ala-pro-lys-val-val.

20. Antibodies raised to an antigenic polypeptide selected from the class consisting of:
(a) met-ala-phe-ala-his-asn-pro-pro-ala-gly-pro-leu-pro-gly-ala;
(b) pro-phe-his-lys-asp-gln-thr-phe-thr-glu-tyr-arg-lys-met-his-gly-gly-ala-val;
(c) pro-phe-his-lys-asp-gln-thr-phe-thr-glu-tyr-arg-lys-met;
(d) asp-asn-thr-arg-thr-ser-gly-asp-asn-ala-pro-val-ser-cys-leu-gly-glu;
(e) arg-leu-ileu-glu-asp-asn-glu-tyr-thr-ala-arg-gln-gly-ala-lys-phe-pro;
(f) trp-arg-arg-asp-pro-glu-glu-arg-pro-thr;
(g) arg-leu-lys-lys-ileu-ser-lys-glu-glu-lys-thr-pro-gly-cys-val-lys-ileu-lys-lys;
(h) asp-leu-pro-ser-arg-thr-val-asp-thr-lys-gln-ala-gln-glu-leu-ala-arg;
(i) met-thr-glu-tyr-lys-leu-val-val-val-gly-ala-ser-gly-val-gly-lys-ser-ala;
(j) glu-asp-ileu-his-gln-tyr-arg-glu-gln-ileu-lys-arg-val-lys-asp-ser-asp-asp;

(k) val-arg-glu-ileu-arg-gln-his-lys-leu-arg-lys-leu-asn-pro-pro-asp-glu-ser-gly-pro;
(l) met-thr-glu-tyr-lys-leu-val-val-val-gly-ala-gly-gly-val-gly-lys-ser-ala;
(m) val-asp-glu-tyr-asp-pro-thr-ileu-glu-asp-ser-tyr-arg-lys-gln-val;
(n) arg-his-ser-thr-ser-ser-ser-glu-gln-glu-arg-glu-gly-gly-arg;
(o) asn-gln-gln-thr-arg-glu-phe-val-glu-lys-gly-gly-arg;
(p) pro-glu-val-gln-lys-pro-leu-his-glu-gln;
(q) ala-ser-pro-tyr-pro-asn-leu-ser-asn-gln-gln-thr-arg;
(r) arg-leu-ileu-ala-glu-lys-glu-gln-leu-arg-arg-arg-arg-glu-gln; and
(s) asn-asn-glu-lys-ala-pro-lys-val-val.

21. Antibodies according to claim 20, labeled with a label capable of providing a detectible signal.

22. Antibodies according to claim 20, labeled with a cytotoxic agent.

* * * * *